United States Patent
Ebata

(10) Patent No.: US 12,414,757 B2
(45) Date of Patent: Sep. 16, 2025

(54) ULTRASOUND DIAGNOSTIC APPARATUS AND CONTROL METHOD FOR ULTRASOUND DIAGNOSTIC APPARATUS

(71) Applicant: FUJIFILM Corporation, Tokyo (JP)

(72) Inventor: Tetsurou Ebata, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 308 days.

(21) Appl. No.: 18/311,611

(22) Filed: May 3, 2023

(65) Prior Publication Data

US 2023/0270410 A1   Aug. 31, 2023

Related U.S. Application Data

(63) Continuation of application No. PCT/JP2021/038863, filed on Oct. 21, 2021.

(30) Foreign Application Priority Data

Nov. 26, 2020   (JP) ................. 2020-195870

(51) Int. Cl.
    A61B 8/00   (2006.01)
(52) U.S. Cl.
    CPC .............. A61B 8/463 (2013.01); A61B 8/469 (2013.01)
(58) Field of Classification Search
    CPC ....... A61B 8/463; A61B 8/469; A61B 8/0833; A61B 8/5223
    See application file for complete search history.

(56) References Cited

U.S. PATENT DOCUMENTS

| | | | | |
|---|---|---|---|---|
| 7,720,693 B2 * | 5/2010 | Funahashi | ............... | G16H 30/20 600/300 |
| 2005/0124888 A1 * | 6/2005 | Jjt Rein | ............... | A61B 8/0833 600/443 |

(Continued)

FOREIGN PATENT DOCUMENTS

| CN | 103202703 A | 7/2013 |
|---|---|---|
| JP | 2001-218769 A | 8/2001 |

(Continued)

OTHER PUBLICATIONS

International Search Report issued in PCT/JP2021/038863; mailed Jan. 11, 2022.

(Continued)

*Primary Examiner* — Baisakhi Roy
(74) *Attorney, Agent, or Firm* — Studebaker Brackett PLLC

(57) ABSTRACT

In an ultrasound diagnostic apparatus and a control method for an ultrasound diagnostic apparatus, a first ultrasound image of one pharyngeal part of left and right pharyngeal parts of a subject is analyzed to detect a region of a swallowing residue in the first ultrasound image. Registration of the first ultrasound image is performed with respect to a second ultrasound image of the other pharyngeal part of the left and right pharyngeal parts of the subject, and a region of the second ultrasound image corresponding to the region of the swallowing residue in the first ultrasound image in which the registration has been performed with respect to the second ultrasound image is determined. Then, a graphic including the region of the second ultrasound image is superimposed on the second ultrasound image and displayed on a monitor.

20 Claims, 7 Drawing Sheets

(56) References Cited

U.S. PATENT DOCUMENTS

| | | | |
|---|---|---|---|
| 2008/0194957 A1* | 8/2008 | Hoctor | A61B 8/483 |
| | | | 600/443 |
| 2009/0257554 A1* | 10/2009 | Parks | A61B 6/12 |
| | | | 378/62 |
| 2011/0125026 A1* | 5/2011 | Neto | A61B 8/42 |
| | | | 600/463 |
| 2016/0225145 A1 | 8/2016 | Nagata | |
| 2017/0061611 A1* | 3/2017 | Ito | A61B 6/463 |
| 2017/0273596 A1* | 9/2017 | Le Reverend | A61B 5/082 |
| 2019/0083000 A1* | 3/2019 | Le Reverend | G01N 33/497 |
| 2020/0105081 A1* | 4/2020 | Huang | G07C 9/00571 |
| 2020/0305759 A1* | 10/2020 | Barash | A61B 5/0816 |
| 2021/0196217 A1* | 7/2021 | Hu | A61B 8/08 |

FOREIGN PATENT DOCUMENTS

| | | |
|---|---|---|
| JP | 2016-143194 A | 8/2016 |
| JP | 2020-089613 A | 6/2020 |

OTHER PUBLICATIONS

International Preliminary Report On Patentability (Chapter I) and Written Opinion of the International Searching Authority issued in PCT/JP2021/038863; issued May 30, 2023.

* cited by examiner

ULTRASOUND DIAGNOSTIC APPARATUS AND CONTROL METHOD FOR ULTRASOUND DIAGNOSTIC APPARATUS

CROSS-REFERENCE TO RELATED APPLICATIONS

This application is a Continuation of PCT International Application No. PCT/JP2021/038863 filed on Oct. 21, 2021, which claims priority under 35 U.S.C. § 119(a) to Japanese Patent Application No. 2020-195870 filed on Nov. 26, 2020. The above applications are hereby expressly incorporated by reference, in their entirety, into the present application.

BACKGROUND OF THE INVENTION

1. Field of the Invention

The present invention relates to an ultrasound diagnostic apparatus that captures an ultrasound image for examining dysphagia, and a control method for the ultrasound diagnostic apparatus.

2. Description of the Related Art

Hitherto, an ultrasound diagnostic apparatus using an ultrasound image has been put to practical use in the medical field. In general, an ultrasound diagnostic apparatus comprises an ultrasound probe incorporating a transducer array, and an information terminal connected to the ultrasound probe, and transmits an ultrasound beam from the ultrasound probe toward a subject to scan the subject, receives an ultrasound echo from the subject through the ultrasound probe, and electrically processes the reception signal to generate an ultrasound image.

In a case of a subject with dysphagia, food may sometimes remain in a pyriform sinus or the like of a pharyngeal part after swallowing. In this case, in a case in which a swallowing residue enters the trachea as it is, aspiration pneumonia may occur. Therefore, observing the swallowing residue in the pyriform sinus is very important in the examination of dysphagia. In a case of examining dysphagia, for example, by scanning the pharyngeal part in a state in which an ultrasound probe is brought into contact with the pharyngeal part of the subject, the pharyngeal part including a pyriform sinus and the like is visualized and the presence or absence of the swallowing residue is confirmed.

Here, there are, for example, JP2020-089613A and the like as reference prior art documents of the present invention. JP2020-089613A describes a method of evaluating swallowing ability by acquiring a plurality of still images constituting an ultrasound video, by using a machine learning model such as you only look once (YOLO) that estimate, from each still image, a subject included in each part of the image for each part to specify positions of the tube wall and food during swallowing, and by further comparing still images arranged in a chronological order to calculate the movement speed of the tube wall and food between the still images.

SUMMARY OF THE INVENTION

Meanwhile, a skilled operation is required for the operation of the ultrasound diagnostic apparatus, and in particular, it is difficult to visualize the pyriform sinus. In addition, in a case of examining dysphagia, it is necessary to examine both the left and right pharyngeal parts, which may pose a problem in which a load on a user (examiner) of the ultrasound diagnostic apparatus is large.

An object of the present invention is to provide an ultrasound diagnostic apparatus and a control method for an ultrasound diagnostic apparatus capable of providing support for reducing a load on a user in specifying a region of a swallowing residue in the left and right pharyngeal parts in a case of examining dysphagia.

In order to achieve the above object, the present invention provides an ultrasound diagnostic apparatus comprising:

an ultrasound probe;

an image generation unit that generates an ultrasound image from a reception signal obtained by transmitting and receiving an ultrasound beam to and from a subject using the ultrasound probe;

a monitor that displays the ultrasound image;

a residue detection unit that analyzes a first ultrasound image of one pharyngeal part of left and right pharyngeal parts of the subject to detect a region of a swallowing residue in the first ultrasound image;

a registration unit that performs registration of the first ultrasound image with respect to a second ultrasound image of the other pharyngeal part of the left and right pharyngeal parts of the subject;

a region determination unit that determines a region of the second ultrasound image corresponding to the region of the swallowing residue in the first ultrasound image in which the registration has been performed with respect to the second ultrasound image; and a display control unit that causes the monitor to display a graphic including the region of the second ultrasound image by superimposing the graphic on the second ultrasound image.

Here, it is preferable that the registration unit performs the registration of the first ultrasound image whose left and right are inverted, with respect to the second ultrasound image.

In addition, it is preferable that an input device that is used for a user to perform an input operation; and an image selection unit that selects the first ultrasound image from among a plurality of frames of ultrasound images of the one pharyngeal part in response to an instruction from the user input via the input device are further provided.

Further, it is preferable that the residue detection unit uses the region of the swallowing residue in the first ultrasound image at a time of a past examination of the same subject as the region of the swallowing residue in the first ultrasound image at a time of a current examination of the same subject in a case in which no swallowing residue is detected in the first ultrasound image.

Further, it is preferable that the display control unit causes the monitor to display a graphic including the region of the swallowing residue in the first ultrasound image at a time of a past examination of the same subject by superimposing the graphic on the first ultrasound image at a time of a current examination of the same subject, and causes the monitor to display a graphic including the region of the swallowing residue in the first ultrasound image at the time of the current examination of the same subject by superimposing the graphic on the second ultrasound image at the time of the current examination of the same subject.

Further, it is preferable that the region determination unit determines the region of the second ultrasound image at a time of a current examination of the same subject, on the basis of the region of the swallowing residue in the first ultrasound image at a time of a past examination of the same subject or the region of the second ultrasound image at the time of the past examination of the same subject, and the region of the swallowing residue in the first ultrasound image at a time of a current examination of the same subject, and that the display control unit causes the monitor to display a graphic including the region of the second ultrasound image at the time of the current examination of the same subject by superimposing the graphic on the second ultrasound image at the time of the current examination of the same subject.

Further, it is preferable that a warning unit that issues a warning in a case in which the registration of the first ultrasound image with respect to the second ultrasound image has failed is further provided.

It is preferable that the residue detection unit further analyzes an image of a region of a predetermined shape that encompasses the region of the second ultrasound image to detect a region of a swallowing residue in the second ultrasound image.

In addition, it is preferable that performing the registration of the first ultrasound image with respect to the second ultrasound image through the registration unit, determining the region of the second ultrasound image corresponding to the region of the swallowing residue in the first ultrasound image, in which the registration has been performed with respect to the second ultrasound image, through the region determination unit, and updating the graphic including the region of the second ultrasound image, which is displayed on the monitor by being superimposed on the second ultrasound image, through the display control unit are repeated for each of a plurality of continuous frames of the second ultrasound image.

Alternatively, it is preferable that performing the registration of the first ultrasound image with respect to the second ultrasound image through the registration unit, determining the region of the second ultrasound image corresponding to the region of the swallowing residue in the first ultrasound image, in which the registration has been performed with respect to the second ultrasound image, through the region determination unit, and updating the graphic including the region of the second ultrasound image, which is displayed on the monitor by being superimposed on the second ultrasound image, through the display control unit are repeated for every predetermined number of frames of the second ultrasound image among a plurality of continuous frames of the second ultrasound image.

Further, it is preferable that the region determination unit once determines the region of the second ultrasound image corresponding to the region of the swallowing residue in the first ultrasound image in which the registration has been performed with respect to the second ultrasound image, and then determines a region of the second ultrasound image in a subsequent frame corresponding to a region of the second ultrasound image in a previous frame, in adjacent frames of the second ultrasound image.

Further, it is preferable that a memory that stores the first ultrasound image and the region of the swallowing residue in the first ultrasound image in association with each other is further provided.

Further, it is preferable that the graphic is a surrounding line surrounding the region of the second ultrasound image.

Further, it is preferable that the graphic is a surrounding line of a predetermined shape that encompasses the region of the second ultrasound image.

Further, it is preferable that the region inside the surrounding line is displayed with the ultrasound image as it is, is subjected to predetermined hatching, is colored in a translucent color, or is displayed with a diagonal line.

Further, it is preferable that the graphic is subjected to predetermined hatching, is colored in a translucent color, or is displayed with a diagonal line, in the region of the second ultrasound image.

In addition, the present invention provides a control method for an ultrasound diagnostic apparatus, comprising:

generating a first ultrasound image from a reception signal obtained by transmitting and receiving an ultrasound beam to and from one pharyngeal part of left and right pharyngeal parts of a subject using an ultrasound probe;

analyzing the first ultrasound image to detect a region of a swallowing residue in the first ultrasound image;

generating a second ultrasound image from a reception signal obtained by transmitting and receiving the ultrasound beam to and from the other pharyngeal part of the left and right pharyngeal parts of the subject using the ultrasound probe;

performing registration of the first ultrasound image with respect to the second ultrasound image;

determining a region of the second ultrasound image corresponding to the region of the swallowing residue in the first ultrasound image in which the registration has been performed with respect to the second ultrasound image; and causing a monitor to display a graphic including the region of the second ultrasound image by superimposing the graphic on the second ultrasound image.

In the present invention, the region of the swallowing residue in the first ultrasound image is detected, and the graphic including the region of the second ultrasound image corresponding to the region of the swallowing residue in the first ultrasound image is superimposed on the second ultrasound image and displayed on the monitor. Therefore, according to the present invention, it is possible to reduce the load on the user in specifying the region of the swallowing residue in the left and right pharyngeal parts.

DESCRIPTION OF THE PREFERRED EMBODIMENTS

Hereinafter, an ultrasound diagnostic apparatus and a control method for an ultrasound diagnostic apparatus of the embodiment of the present invention will be described in detail on the basis of suitable embodiments shown in the accompanying drawings.

Figure 1:
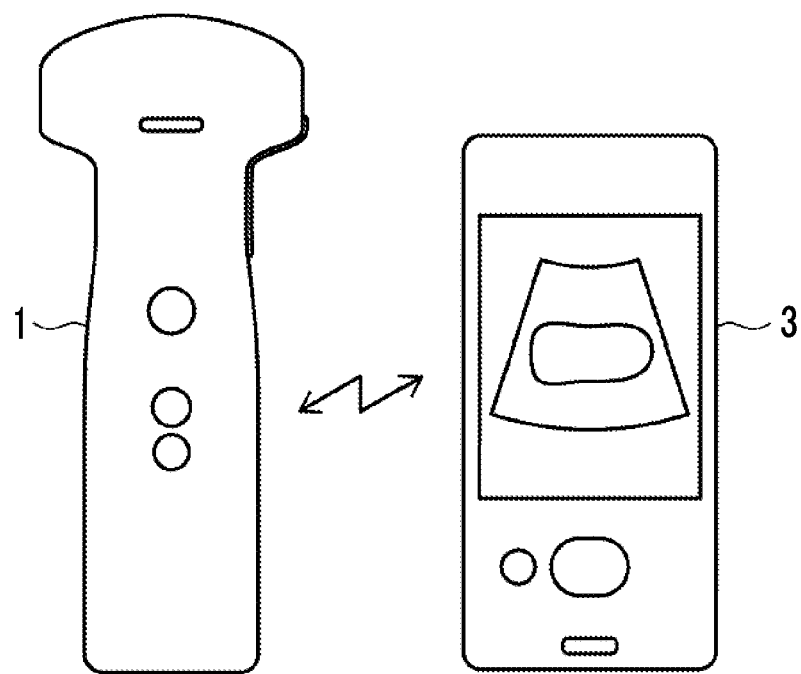
FIG. 1 is a conceptual diagram showing a configuration of an ultrasound diagnostic apparatus according to one embodiment of the present invention.

FIG. 1 is a conceptual diagram showing a configuration of the ultrasound diagnostic apparatus according to one embodiment of the present invention. The ultrasound diagnostic apparatus shown in FIG. 1 comprises an ultrasound probe 1 and a handheld type information terminal 3 connected to the ultrasound probe 1 by wire or wirelessly. The ultrasound diagnostic apparatus of the present embodiment is realized by the ultrasound probe 1, the handheld type information terminal 3, and an ultrasound diagnosis application program that operates on the information terminal 3.

Figure 2:
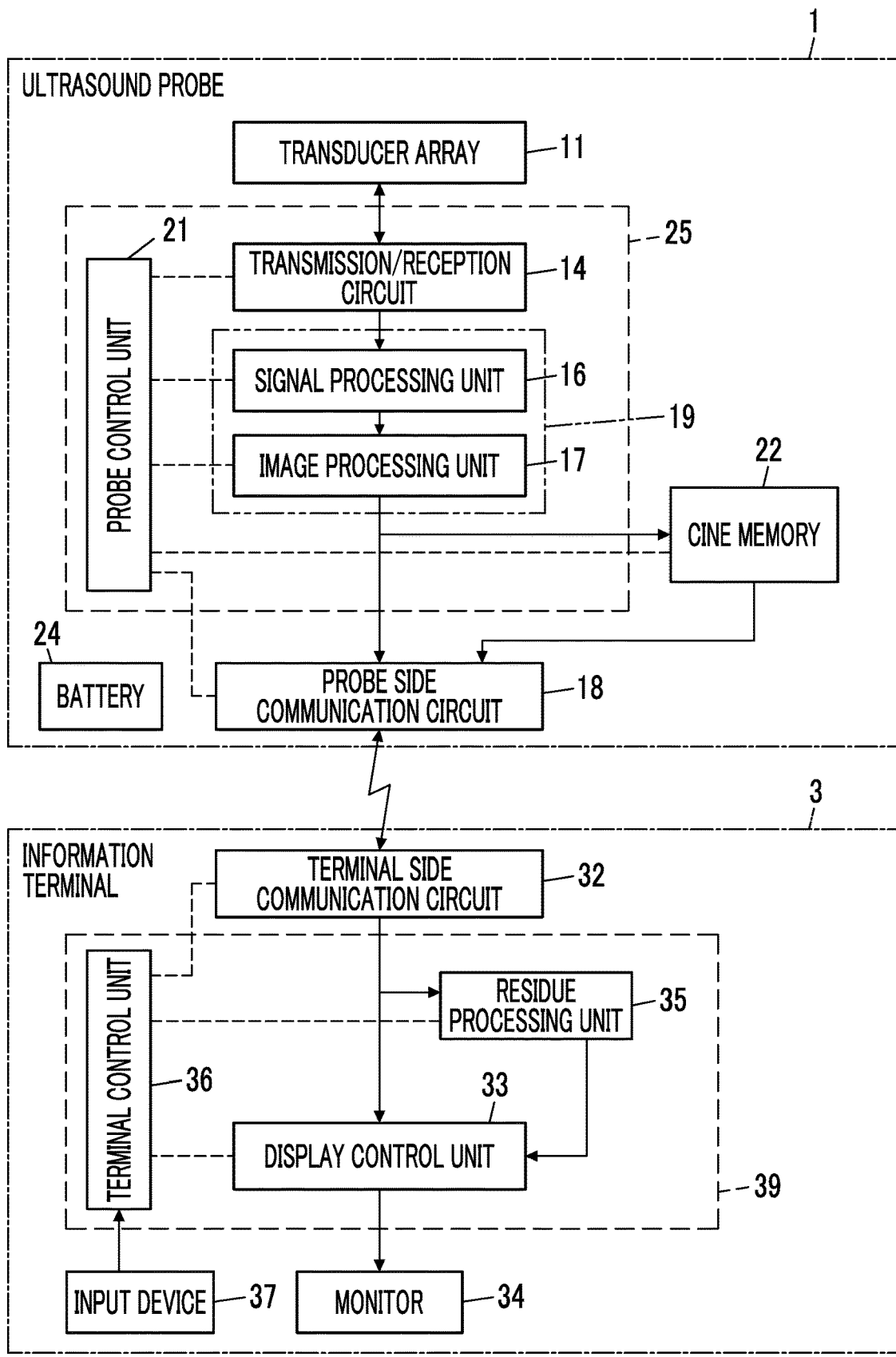
FIG. 2 is a block diagram showing configurations of an ultrasound probe and an information terminal.

The ultrasound probe 1 scans a subject with an ultrasound beam, captures an ultrasound image, and outputs data corresponding to the ultrasound image, that is, image information data of the ultrasound image in the case of the present embodiment. As shown in FIG. 2, the ultrasound probe 1 comprises a transducer array 11, a transmission/reception circuit 14, a signal processing unit 16, an image processing unit 17, a probe side communication circuit 18, a probe control unit 21, a cine memory 22, and a battery 24.

The transmission/reception circuit 14 is bidirectionally connected to the transducer array 11. The signal processing unit 16, the image processing unit 17, and the probe side communication circuit 18 are sequentially connected in series to the transmission/reception circuit 14. The signal processing unit 16 and the image processing unit 17 constitute an image information data generation unit 19. Further, the cine memory 22 is connected to the image processing unit 17, and the probe side communication circuit 18 is connected to the cine memory 22.

In addition, the probe control unit 21 is connected to the transmission/reception circuit 14, the signal processing unit 16, the image processing unit 17, the cine memory 22, and the probe side communication circuit 18. Further, the ultrasound probe 1 incorporates the battery 24.

A probe side processor 25 is composed of the transmission/reception circuit 14, the image information data generation unit 19 (the signal processing unit 16 and the image processing unit 17), and the probe control unit 21.

The transducer array 11 has a plurality of ultrasound transducers arranged one-dimensionally or two-dimensionally. Each of these transducers transmits an ultrasound wave in accordance with a drive signal supplied from the transmission/reception circuit 14 and outputs an analog reception signal by receiving a reflected wave from the subject.

Each transducer is formed of, for example, an element obtained by forming electrodes at both ends of a piezoelectric body containing piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 3:
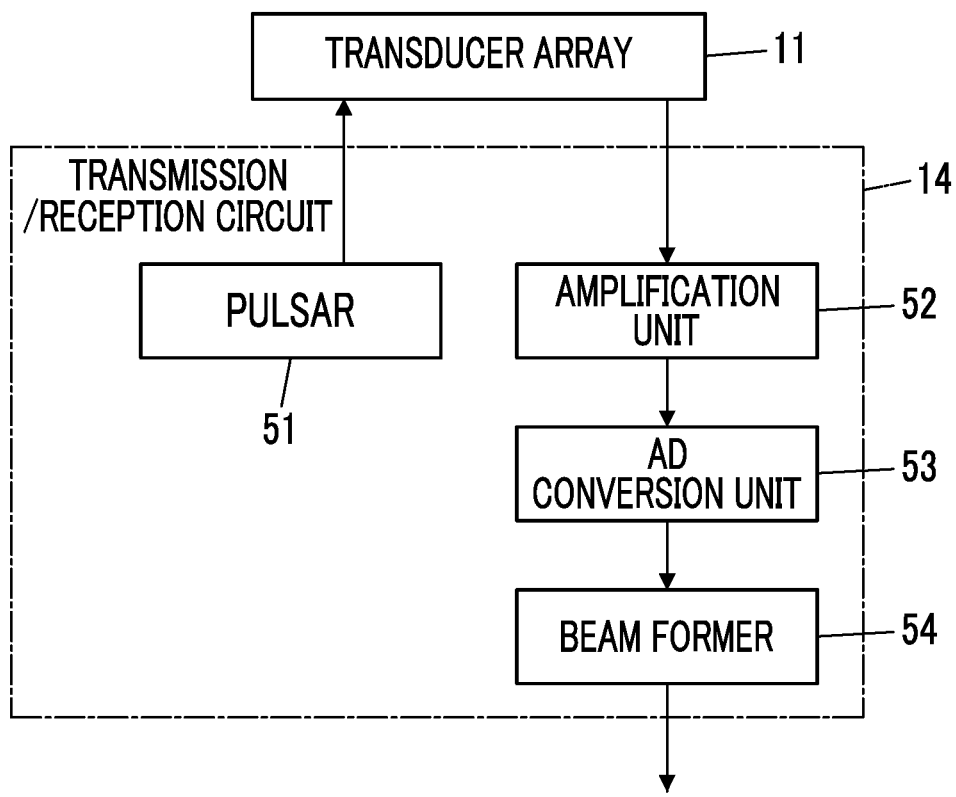
FIG. 3 is a block diagram showing a configuration of a transmission/reception circuit.

Under the control of the probe control unit 21, the transmission/reception circuit 14 transmits ultrasound waves from the transducer array 11 and performs reception focus processing on a reception signal output from the transducer array 11, which has received an ultrasound echo, to generate a sound ray signal. As shown in FIG. 3, the transmission/reception circuit 14 includes a pulsar 51 connected to the transducer array 11, an amplification unit 52, an analog-to-digital (AD) conversion unit 53, and a beam former 54 that are sequentially connected in series to the transducer array 11.

The pulsar 51 includes, for example, a plurality of pulse generators, and supplies respective drive signals to the plurality of transducers by adjusting amounts of delay such that ultrasound waves transmitted from the plurality of transducers of the transducer array 11 form an ultrasound beam, on the basis of a transmission delay pattern selected by the probe control unit 21. In this manner, in a case in which a pulsed or continuous-wave voltage is applied to the electrodes of the transducer of the transducer array 11, the piezoelectric body expands and contracts, and a pulsed or continuous-wave ultrasound wave is generated from each of the transducers, whereby the ultrasound beam is formed from a combined wave of these ultrasound waves.

The transmitted ultrasound beam is reflected in a target, for example, a site of the subject, and propagates toward the transducer array 11 of the ultrasound probe 1. Each of the transducers constituting the transducer array 11 expands and contracts by receiving the ultrasound echo propagating toward the transducer array 11 in this way, generates a reception signal, which is an electrical signal, and outputs the reception signal to the amplification unit 52.

The amplification unit 52 amplifies the signal input from each of the transducers constituting the transducer array 11 and transmits the amplified signal to the AD conversion unit 53. The AD conversion unit 53 converts the signal transmitted from the amplification unit 52 into digital reception data and outputs the reception data to the beam former 54.

The beam former 54 performs so-called reception focus processing by giving and adding delay with respect to each reception data converted by the AD conversion unit 53, in accordance with a sound speed or a sound speed distribution set on the basis of a reception delay pattern selected by the probe control unit 21. By this reception focus processing, each reception data converted by the AD conversion unit 53 is phase-added, and a sound ray signal in which the focus of the ultrasound echo is narrowed down is generated.

The image information data generation unit 19 generates image information data on the basis of the sound ray signal generated by the transmission/reception circuit 14. As described above, the image information data generation unit 19 includes the signal processing unit 16 and the image processing unit 17.

Under the control of the probe control unit 21, the signal processing unit 16 generates image signal data before image formation into an ultrasound image on the basis of the sound ray signal generated by the transmission/reception circuit 14. More specifically, the signal processing unit 16 performs signal processing on the sound ray signal generated by the beam former 54 of the transmission/reception circuit 14, for example, correction of attenuation caused by the propagation distance based on the depth of the position where the ultrasound wave is reflected, and then performs envelope detection processing to generate a signal representing tomographic image information regarding the tissue inside the subject as image signal data before image formation.

Under the control of the probe control unit 21, the image processing unit 17 generates an ultrasound image as the image information data generated by the image information data generation unit 19 on the basis of the image signal data generated by the signal processing unit 16. More specifically, the image processing unit 17 raster-converts the image signal data before image formation generated by the signal processing unit 16 into an image signal in accordance with a scanning method of a normal television signal, and performs various types of image processing, such as brightness correction, tone correction, sharpness correction, image size correction, refresh rate correction, scanning frequency correction, and color correction in accordance with the display format of a monitor 34, with respect to the image signal converted in this manner, to generate the ultrasound image (ultrasound image signal), and then outputs the ultrasound image generated by the image information data generation unit 19 as the image information data to the probe side communication circuit 18.

The transmission/reception circuit 14, the signal processing unit 16, and the image processing unit 17 constitute an image generation unit of the embodiment of the present invention.

The image generation unit generates the ultrasound image, that is, the ultrasound image as the image information data in the case of the present embodiment, from the reception signal obtained by transmitting and receiving the ultrasound beam to and from the subject using the ultrasound probe 1 (more precisely, the transducer array 11).

The cine memory 22 stores the image information data generated by the image information data generation unit 19 under the control of the probe control unit 21. More specifically, in a case of a live mode, the cine memory 22 stores the ultrasound image generated by the image processing unit 17 of the image information data generation unit 19 as the image information data. The cine memory 22 has a memory capacity for storing ultrasound images generated over a period of several seconds to several tens of seconds, for example, in a case in which 30 frames of ultrasound images are captured for one second, several tens of frames to several hundreds of frames of ultrasound images.

The cine memory 22 is a ring buffer. Therefore, in a case in which the ultrasound images of the past frames having the number of frames corresponding to the memory capacity are stored in the cine memory 22, the latest frames of ultrasound images are sequentially stored in the cine memory 22 instead of the oldest frames of ultrasound images. As a result, in the cine memory 22, the ultrasound images of the past frames having the number of frames corresponding to the memory capacity are constantly stored from the ultrasound image of the latest frame.

Here, the live mode is a mode in which ultrasound images (video images) captured at a constant frame rate are sequentially displayed (real-time display).

A freeze mode is a mode in which ultrasound images (video images) captured in the case of the live mode are stored in the cine memory 22 and any frame of ultrasound image (still image) is read out from among the past frames of ultrasound images (video images) stored in the cine memory 22 and is displayed.

Under the control of the probe control unit 21, the probe side communication circuit 18 transmits the image information data generated by the image processing unit 17 or the image information data stored in the cine memory 22 by wire or wirelessly. In the case of the present embodiment, the probe side communication circuit 18 includes an antenna for transmitting and receiving radio waves, and modulates carriers on the basis of the ultrasound image generated by the image processing unit 17 to generate a transmission signal and supplies the transmission signal to the antenna to transmit radio waves from the antenna, thereby wirelessly transmitting the ultrasound image.

As a carrier modulation method, amplitude shift keying (ASK), phase shift keying (PSK), quadrature phase shift keying (QPSK), 16 quadrature amplitude modulation (16QAM), or the like is used.

In addition, the probe side communication circuit 18 can also connect the ultrasound probe 1 and the information terminal 3 with a cable such as a universal serial bus (USB) cable.

The probe side communication circuit 18 wirelessly transmits the image information data of the frames generated by the image information data generation unit 19 in the case of the live mode and wirelessly transmits the image information data stored in the cine memory 22 in the case of the freeze mode.

The probe control unit 21 controls each unit of the ultrasound probe 1 on the basis of a program or the like stored in advance. More specifically, the probe control unit 21 controls the transmission/reception circuit 14 such that the transmission of the ultrasound beam and the reception of the ultrasound echo are performed on the basis of an examination mode and a scanning method set in advance. In addition, the probe control unit 21 controls the signal processing unit 16 and the image processing unit 17 of the image information data generation unit 19 such that signal processing set in advance is performed on the sound ray signal and image processing set in advance is performed on the image signal data. The probe control unit 21 performs control such that the image information data generated by the image information data generation unit 19 is stored in the cine memory 22 in the case of the live mode and the past frame of ultrasound image stored in the cine memory 22 is read out in the case of the freeze mode. Further, the probe control unit 21 controls the probe side communication circuit 18 such that the image signal data is transmitted with the transmission radio wave intensity set in advance.

Here, the examination mode refers to any of examination modes that can be used in the ultrasound diagnostic apparatus, such as a brightness (B) mode, a color doppler (CF) mode, a power doppler (PD) mode, a motion (M) mode, a pulse doppler (PW) mode, and a continuous wave doppler (CW) mode, and the scanning method refers to any of the scanning methods, such as an electronic sector scanning method, an electronic linear scanning method, and an electronic convex scanning method.

The battery 24 is incorporated in the ultrasound probe 1 and supplies power to each circuit of the ultrasound probe 1.

Next, the information terminal 3 is a handheld type terminal device, such as a smartphone and a tablet personal computer (PC), and displays the ultrasound image on the basis of data corresponding to the ultrasound image captured by the ultrasound probe 1. As shown in FIG. 2, the information terminal 3 comprises a terminal side communication circuit 32, a display control unit 33, a residue processing unit 35, a terminal control unit 36, the monitor 34, and an input device 37.

The display control unit 33 and the monitor 34 are sequentially connected in series to the terminal side communication circuit 32. In addition, the residue processing unit 35 is connected to the terminal side communication circuit 32, and the display control unit 33 is connected to the residue processing unit 35. The terminal control unit 36 is connected to the terminal side communication circuit 32, the display control unit 33, and the residue processing unit 35, and the input device 37 is connected to the terminal control unit 36.

In the case of the present embodiment, the probe side communication circuit 18 of the ultrasound probe 1 and the terminal side communication circuit 32 of the information terminal 3 are wirelessly connected to each other by wireless communication, whereby the ultrasound probe 1 and the information terminal 3 are connected such that information can be bidirectionally exchanged.

Under the control of the terminal control unit 36, the terminal side communication circuit 32 receives the image information data transmitted from the probe side communication circuit 18 of the ultrasound probe 1 by wire or wirelessly. In the case of the present embodiment, the terminal side communication circuit 32 includes an antenna for transmitting and receiving radio waves, and receives a transmission signal wirelessly transmitted from the probe side communication circuit 18 via the antenna to demodulate the received transmission signal, thereby outputting the ultrasound image (ultrasound image signal), which is the image information data.

The display control unit 33 causes the monitor 34 to display various types of information under the control of the terminal control unit 36. For example, the display control unit 33 performs predetermined processing on the ultrasound image, which is the image information data received by the terminal side communication circuit 32, and causes the monitor 34 to display the ultrasound image. In addition, the display control unit 33 causes the monitor 34 to display a graphic including a region of a second ultrasound image, which will be described later, by superimposing the graphic on the second ultrasound image, or causes the monitor 34 to display a warning message, various operation screens, and the like.

The monitor 34 displays various types of information. The monitor 34 displays, in addition to the ultrasound image, the region of the second ultrasound image, which will be described later, a warning message, various operation screens, and the like, under the control of the display control unit 33. Examples of the monitor 34 include a liquid crystal display (LCD) and an organic electro-luminescence (EL) display.

The input device 37 is used for the user to perform an input operation to input various instructions, and in the case of the present embodiment, includes a touch panel or the like on which the user can perform a touch operation to input various instructions.

Figure 4:
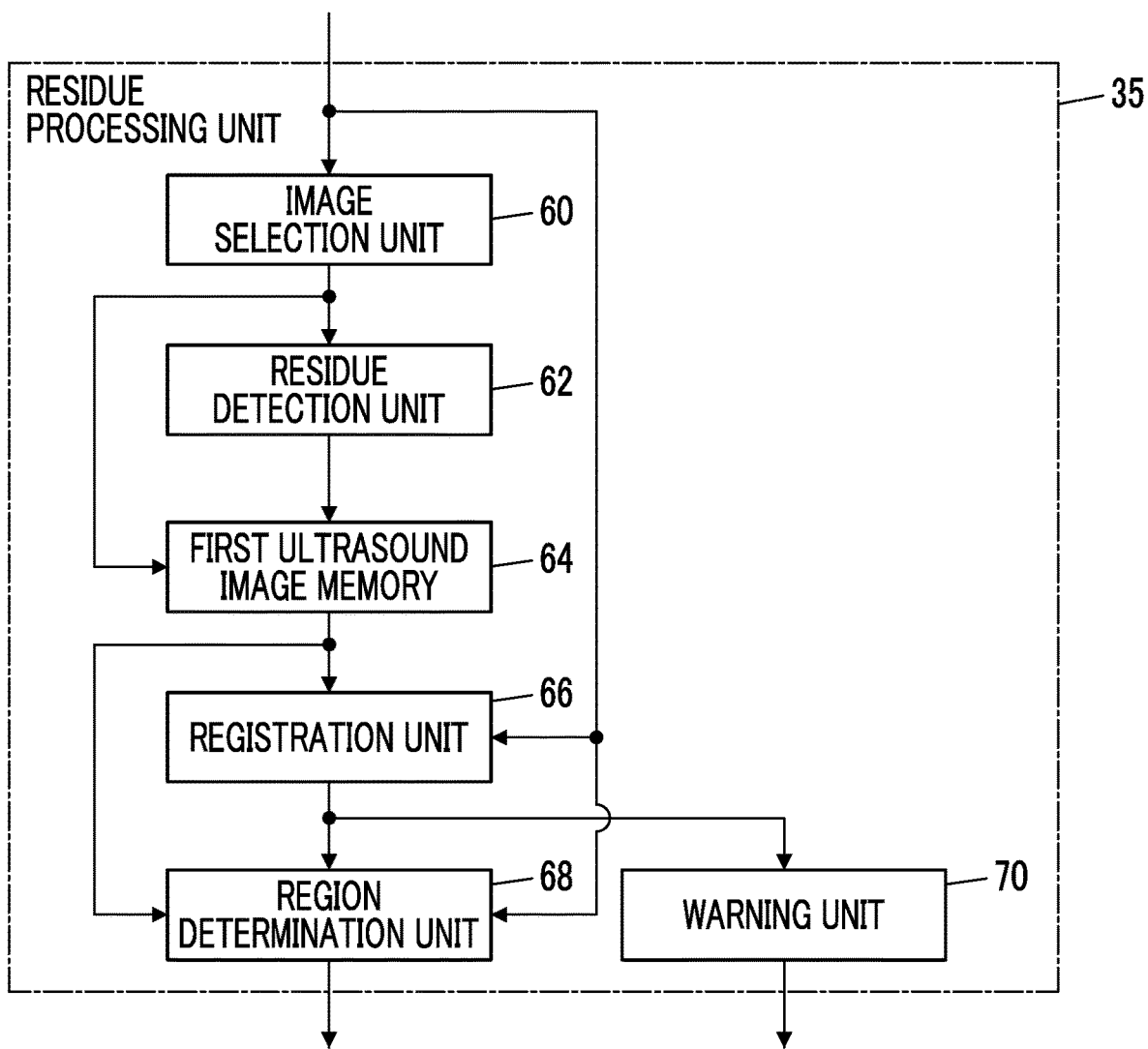
FIG. 4 is a block diagram showing a configuration of a residue processing unit.

Under the control of the terminal control unit 36, the residue processing unit 35 performs various types of processing related to food remaining in a pharyngeal part of the subject, for example, a pyriform sinus, that is, a swallowing residue, during swallowing. As shown in FIG. 4, the residue processing unit 35 comprises an image selection unit 60, a residue detection unit 62, a first ultrasound image memory 64, a registration unit 66, a region determination unit 68, and a warning unit 70.

The residue detection unit 62, the first ultrasound image memory 64, the registration unit 66, and the region determination unit 68 are sequentially connected in series to the image selection unit 60. In addition, the first ultrasound image memory 64 is connected to the image selection unit 60, and the region determination unit 68 is connected to the first ultrasound image memory 64. Further, the warning unit 70 is connected to the registration unit 66.

The image selection unit 60 selects a first ultrasound image, which is one frame of ultrasound image, from among the plurality of frames of ultrasound images of one pharyngeal part of left and right pharyngeal parts of the subject in response to an instruction from the user input via the input device 37.

The image selection unit 60 can select, as the first ultrasound image, one frame of ultrasound image (still image) acquired at the timing when the user presses a freeze button, from among the ultrasound images (video images) captured in the case of the live mode. Alternatively, in the case of the freeze mode, the image selection unit 60 may select, as the first ultrasound image, one frame of ultrasound image (still image) designated by the user from among the past ultrasound images (video images) stored in the cine memory 22.

The residue detection unit 62 detects the presence or absence of a swallowing residue and a region thereof by analyzing the first ultrasound image, which is the ultrasound image of one pharyngeal part. For example, although the residue detection unit 62 detects the presence or absence of the swallowing residue and the region thereof in the pyriform sinus by analyzing the first ultrasound image including the pyriform sinus, the residue detection unit 62 may detect the presence or absence of the swallowing residue and the region thereof in a site other than the pyriform sinus.

Although the present invention is not particularly limited, the residue detection unit 62 can detect the presence or absence of the swallowing residue and the region thereof in the first ultrasound image by using at least one of a determination model that has been trained using a machine learning technique such as deep learning, template matching, or an image analysis technique using a feature amount, such as adaptive boosting (Adaboost), support vector machine (SVM), or scale-invariant feature transform (SIFT).

Here, the determination model is a pre-trained model that has learned the relationship between a training ultrasound image, in which one pharyngeal part is captured, and the presence or absence of the swallowing residue and the region thereof in the training ultrasound image by using the training ultrasound image and the presence or absence of the swallowing residue and the region thereof in the training ultrasound image as teacher data, for a plurality of pieces of the teacher data.

The determination model receives the first ultrasound image as an input and outputs a result of estimating the presence or absence of the swallowing residue and the region thereof in the first ultrasound image.

The first ultrasound image memory 64 is a memory that stores the first ultrasound image selected by the image selection unit 60 and the region of the swallowing residue in the first ultrasound image detected by the residue detection unit 62 in association with each other.

The registration unit 66 performs registration of the first ultrasound image stored in the first ultrasound image memory 64 with respect to the second ultrasound image, which is an ultrasound image of the other pharyngeal part of the left and right pharyngeal parts of the subject generated in real time.

Although the present invention is not particularly limited, the registration unit 66 can perform the registration of the first ultrasound image with respect to the second ultrasound image by using a known technique such as rigid/non-rigid registration.

The region determination unit 68 determines the region of the second ultrasound image corresponding to the region of the swallowing residue in the first ultrasound image in which the registration has been performed with respect to the second ultrasound image.

The warning unit 70 issues a warning to the user in a case in which the registration of the first ultrasound image with respect to the second ultrasound image has failed.

The warning unit 70 may display the warning message on the monitor 34 through the display control unit 33, may read a message aloud to output the message from the speaker, or may perform both at the same time.

The terminal control unit 36 controls each unit of the information terminal 3 on the basis of a program stored in advance, an instruction from the user input through the input device 37, and the like. More specifically, the terminal control unit 36 controls the terminal side communication circuit 32 such that the transmission signal is received from the probe side communication circuit 18 of the ultrasound probe 1. In addition, the terminal control unit 36 controls the display control unit 33 such that the ultrasound image is displayed on the monitor 34 on the basis of the image information data. Further, the terminal control unit 36 controls the residue processing unit 35 such that various types of processing related to the swallowing residue are performed.

The display control unit 33, the residue processing unit 35, and the terminal control unit 36 constitute a terminal side processor 39.

Figure 5:
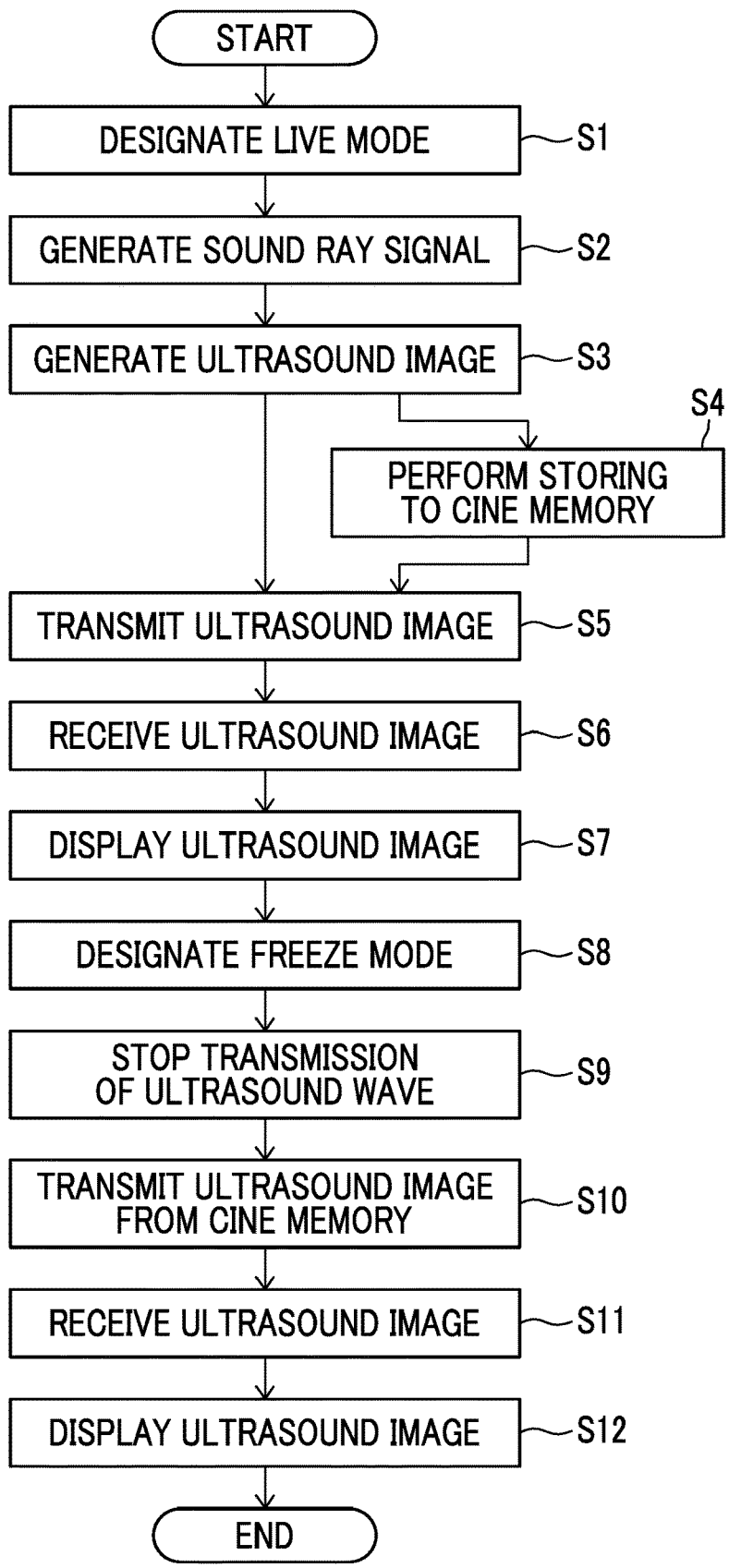
FIG. 5 is a flowchart of one embodiment showing an operation of the ultrasound diagnostic apparatus in a case in which an ultrasound image is captured.

Next, the operation of the ultrasound diagnostic apparatus in a case of capturing the ultrasound image will be described with reference to the flowchart of FIG. 5. First, the operation of the ultrasound diagnostic apparatus in the case of the live mode will be described.

In a case in which the live mode is designated on the basis of the instruction input from the user through the input device 37 (step S1), transmission of ultrasound waves is started by the transmission/reception circuit 14 in a state in which the ultrasound probe 1 is in contact with the body surface of the subject, and the sound ray signal is generated (step S2).

That is, under the control of the probe control unit 21, the ultrasound beam is transmitted into the subject from the plurality of transducers of the transducer array 11 in accordance with the drive signal from the pulsar 51 of the transmission/reception circuit 14.

The ultrasound echo from the subject based on the ultrasound beam transmitted from the pulsar 51 is received by each transducer of the transducer array 11, and the reception signal, which is an analog signal, is output from each transducer of the transducer array 11 that has received the ultrasound echo.

The reception signal, which is an analog signal output from each transducer of the transducer array 11, is amplified by the amplification unit 52 of the transmission/reception circuit 14 and is AD-converted by the AD conversion unit 53, whereby reception data is acquired.

The sound ray signal is generated by performing reception focus processing on the reception data through the beam former 54.

Subsequently, the image information data generation unit 19 generates the ultrasound image as the image information data on the basis of the sound ray signal generated by the beam former 54 of the transmission/reception circuit 14 (step S3).

That is, the sound ray signal generated by the beam former 54 is subjected to various types of signal processing by the signal processing unit 16 of the image information data generation unit 19, and a signal representing tomographic image information regarding the tissue inside the subject is generated as the image signal data before image formation.

The image signal data generated by the signal processing unit 16 is raster-converted by the image processing unit 17 and further subjected to various types of image processing, whereby the ultrasound image as the image information data is generated.

The ultrasound image generated by the image processing unit 17 is stored in the cine memory 22 (step S4).

In addition, the ultrasound image generated by the image processing unit 17 is wirelessly transmitted from the probe side communication circuit 18 toward the information terminal 3 (step S5).

Subsequently, the ultrasound image wirelessly transmitted from the probe side communication circuit 18 of the ultrasound probe 1 is received by the terminal side communication circuit 32 under the control of the terminal control unit 36 of the information terminal 3 (step S6).

Subsequently, the ultrasound image received by the terminal side communication circuit 32 is subjected to predetermined processing by the display control unit 33 and displayed on the monitor 34 (step S7).

Next, the operation of the ultrasound diagnostic apparatus in the case of the freeze mode will be described.

In a case in which the freeze mode is designated on the basis of the instruction from the user input through the input device 37 (step S8), the transmission of the ultrasound wave from the transducer array 11 is stopped (step S9).

In this case, as the image information data, the past frame of ultrasound image stored in the cine memory 22 is read out and wirelessly transmitted from the probe side communication circuit 18 (step S10).

Subsequently, the terminal side communication circuit 32 receives the ultrasound image wirelessly transmitted from the probe side communication circuit 18 (step S11).

Subsequently, the display control unit 33 displays the past frame of ultrasound image received by the terminal side communication circuit 32 on the monitor 34 (step S12).

Figure 6:
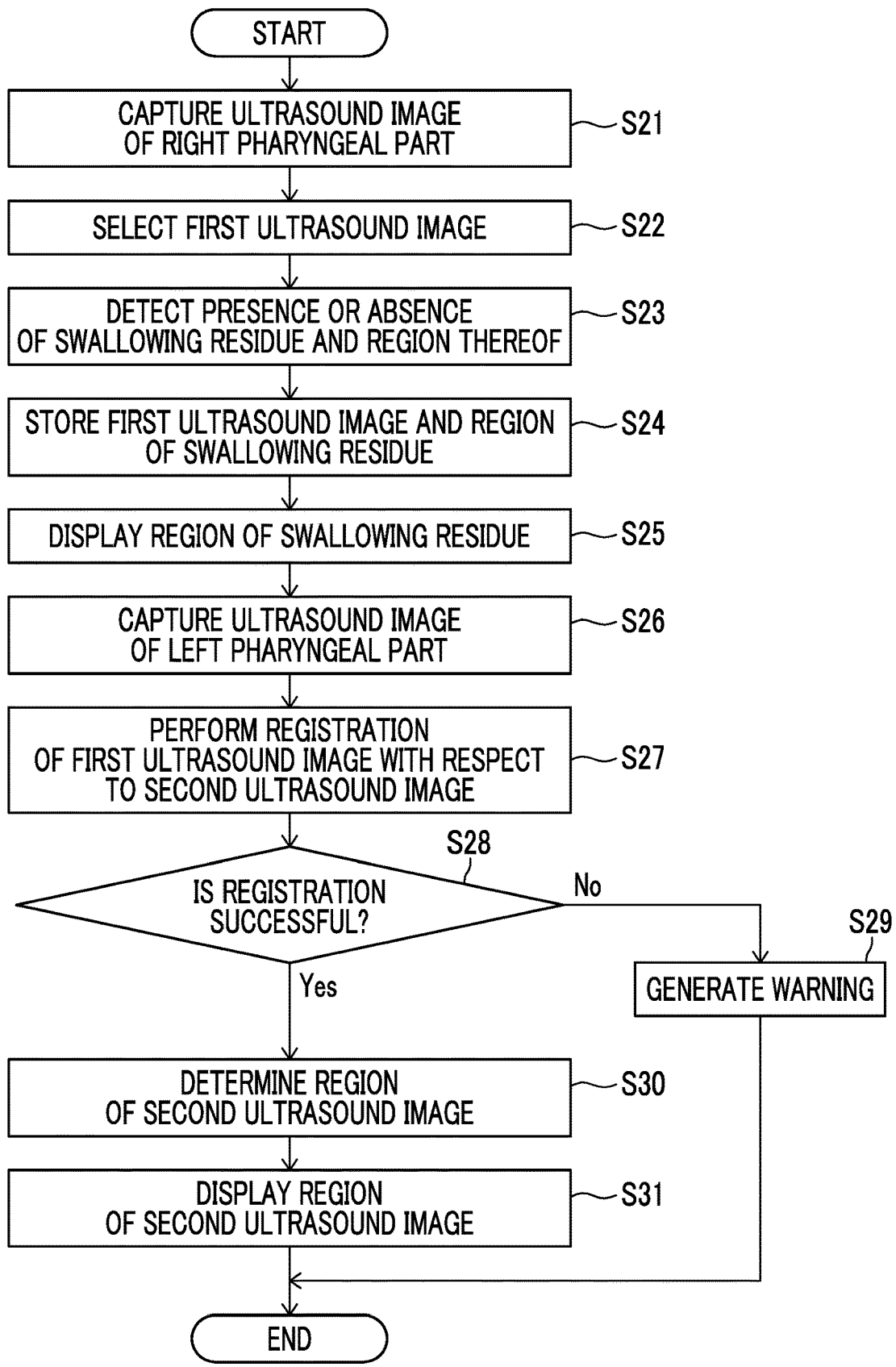
FIG. 6 is a flowchart of one embodiment showing an operation of the ultrasound diagnostic apparatus in a case in which dysphagia is examined.

Next, an operation of the ultrasound diagnostic apparatus in a case of examining dysphagia will be described with reference to the flowchart of FIG. 6.

First, the user captures the ultrasound image of one of the left and right pharyngeal parts of the subject, for example, the right pharyngeal part (step S21).

In this case, in a state in which the ultrasound probe 1 is in contact with the right pharyngeal part of the subject, transmission of ultrasound waves is started by the transmission/reception circuit 14, and the sound ray signal is generated.

Subsequently, the image information data generation unit 19 generates the ultrasound image (video image) in which the right pharyngeal part is captured on the basis of the sound ray signal generated by the transmission/reception circuit 14.

The ultrasound image of the right pharyngeal part generated by the image information data generation unit 19 is stored in the cine memory 22.

In addition, the ultrasound image of the right pharyngeal part is transmitted from the ultrasound probe 1 to the information terminal 3 and received by the terminal side communication circuit 32 of the information terminal 3.

Subsequently, the ultrasound image received by the terminal side communication circuit 32 is subjected to predetermined processing by the display control unit 33 and displayed on the monitor 34.

Subsequently, the user selects, from among a plurality of frames of ultrasound images of the right pharyngeal part, the first ultrasound image that is one frame of ultrasound image for detecting the presence or absence of the swallowing residue and the region thereof in the right ultrasound image (step S22).

In this case, in response to the instruction from the user input via the input device 37, the image selection unit 60 selects, from among the plurality of frames of ultrasound images of the right pharyngeal part, the first ultrasound image that is one frame of ultrasound image.

In a case in which the first ultrasound image is selected, the residue detection unit 62 analyzes the first ultrasound image to detect the presence or absence of the swallowing residue and the region thereof in the first ultrasound image (step S23). For example, the presence or absence of the swallowing residue in the pyriform sinus is detected, and in a case in which there is the swallowing residue, the region thereof is detected. The first ultrasound image and the region of the swallowing residue in the first ultrasound image are stored in the first ultrasound image memory 64 in association with each other (step S24).

Figure 7:
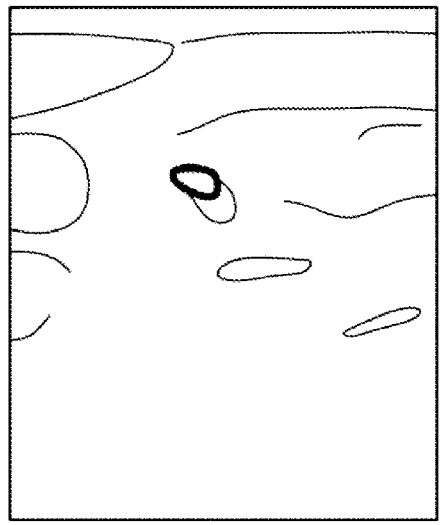
FIG. 7 is a conceptual diagram of one embodiment showing a region of a swallowing residue in a first ultrasound image in which a right pharyngeal part is captured.

In addition, in a case in which the region of the swallowing residue in the first ultrasound image is detected, the display control unit 33 causes the monitor 34 to display the graphic including the region of the swallowing residue in the first ultrasound image by superimposing the graphic on the first ultrasound image (step S25). For example, as shown in FIG. 7, a surrounding line surrounding the region of the swallowing residue is superimposed on the first ultrasound image and displayed on the monitor 34. As a result, the user can visually confirm the presence or absence of the swallowing residue and the region thereof in the first ultrasound image.

Subsequently, the display control unit 33 displays, for example, a message "Please start scanning the other pharyngeal part" on the monitor 34. This prompts the user to start capturing the ultrasound image of the other pharyngeal part of the left and right pharyngeal parts, for example, the left pharyngeal part.

In response to this, the user captures the ultrasound image of the left pharyngeal part (step S26).

The operation in this case is the same as that in a case in which the ultrasound image of the right pharyngeal part is captured. That is, in a state in which the ultrasound probe 1 is in contact with the left pharyngeal part of the subject, the second ultrasound image (video image) which is the ultrasound image of the left pharyngeal part is generated. The second ultrasound image is stored in the cine memory 22. In addition, the second ultrasound image is transmitted from the ultrasound probe 1 to the information terminal 3 and displayed on the monitor 34 by the display control unit 33.

In a case in which the second ultrasound image is captured, the registration unit 66 performs registration of the first ultrasound image stored in the first ultrasound image memory 64 with respect to the second ultrasound image (step S27). In the case of the present embodiment, the registration unit 66 inverts the left and right of the first ultrasound image in which the right pharyngeal part is captured, and performs registration of the first ultrasound image whose left and right are inverted, with respect to the second ultrasound image in which the left pharyngeal part is captured.

Here, in a case in which the registration has failed (No in step S28), for example, in a case in which the registration continues to fail a predetermined number of times, the warning unit 70 issues a warning for notifying the user of the failure in the registration (step S29). In this case, since there is a probability of an inappropriate cross-section being visualized in the first ultrasound image or the second ultrasound image, no further processing is performed, but the second ultrasound image being examined is continuously displayed on the monitor 34.

On the other hand, in a case in which the registration is successful (Yes in step S28), the region determination unit 68 determines the region of the second ultrasound image corresponding to the region of the swallowing residue in the first ultrasound image in which the registration has been performed with respect to the second ultrasound image (step S30).

Figure 8A:
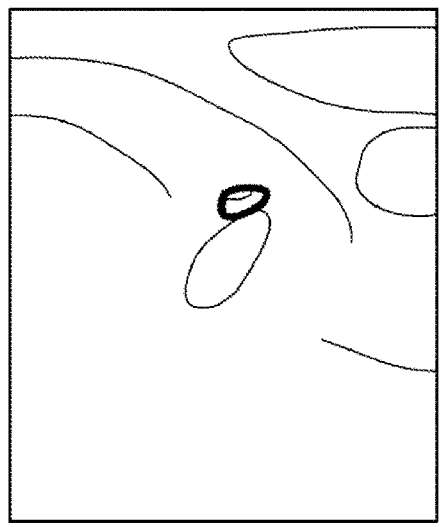
FIG. 8A is a conceptual diagram of one embodiment showing a region of a second ultrasound image in which a left pharyngeal part is captured, which corresponds to the region of the swallowing residue in the first ultrasound image.

In a case in which the region of the second ultrasound image is determined, the graphic including the region of the second ultrasound image is superimposed on the second ultrasound image and displayed on the monitor 34 by the display control unit 33 (step S31). For example, as shown in FIG. 8A, the surrounding line surrounding the region of the second ultrasound image is superimposed on the second ultrasound image and displayed on the monitor 34. Since the registration of the first ultrasound image whose left and right are inverted is performed with respect to the second ultrasound image, the region of the second ultrasound image shown in FIG. 8A has a shape in which the left and right of the region of the swallowing residue in the first ultrasound image shown in FIG. 7 are inverted. As a result, the user can visually confirm the region having a probability of being the swallowing residue, in the second ultrasound image.

As described above, in the ultrasound diagnostic apparatus, the region of the swallowing residue in the first ultrasound image is detected, and the graphic including the region of the second ultrasound image corresponding to the region of the swallowing residue in the first ultrasound image is superimposed on the second ultrasound image and displayed on the monitor 34. Therefore, in the ultrasound diagnostic apparatus, it is possible to reduce the load on the user in specifying the region of the swallowing residue in the left and right pharyngeal parts.

In addition, in the ultrasound diagnostic apparatus, the graphic including the region of the second ultrasound image corresponding to the region of the swallowing residue in the first ultrasound image is superimposed on the second ultrasound image and displayed, so that it is not necessary to sequentially detect the region of the swallowing residue in the second ultrasound image generated in real time. Therefore, even in a case in which the processing capacity of the information terminal 3 is relatively low, the ultrasound diagnostic apparatus can easily display the region having a probability of being the swallowing residue, in the second ultrasound image.

The ultrasound image of the left pharyngeal part is captured after the ultrasound image of the right pharyngeal part of the subject is captured. On the contrary, the ultrasound image of the right pharyngeal part may be captured after the ultrasound image of the left pharyngeal part is captured.

Figure 8B:
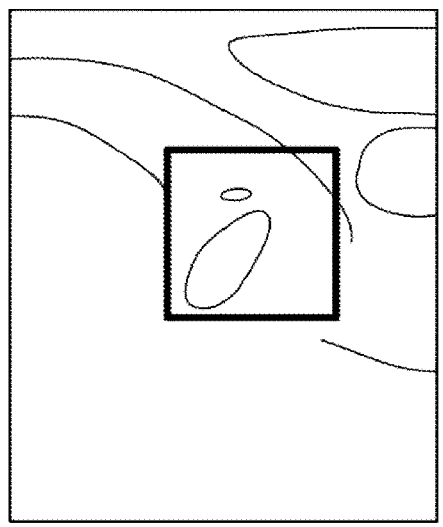
FIG. 8B is a conceptual diagram of another embodiment showing the region of the second ultrasound image in which the left pharyngeal part is captured, which corresponds to the region of the swallowing residue in the first ultrasound image.

The display control unit 33 may cause the monitor 34 to display, instead of the surrounding line surrounding the region of the second ultrasound image, the surrounding line of a predetermined shape that encompasses the region of the second ultrasound image. The brightness, color, line type, shape, and the like of the surrounding line are not particularly limited. For example, the line type may be a solid line, a dotted line, or the like. In addition, the surrounding line may be a straight line or a curved line. The shape of the surrounding line may be a shape obtained by enlarging the size while maintaining the same shape as the region of the second ultrasound image, a circular shape, or a rectangle as shown in FIG. 8B. Specifically, a rectangle in which the region of the second ultrasound image is inscribed (a circumscribed rectangle of the region of the second ultrasound image) may be used, a rectangle in which the region of the shape obtained by enlarging the size while maintaining the same shape as the region of the second ultrasound image is inscribed, a circular shape in which the region is inscribed in the same manner as the rectangle, or the like. In addition, in a case in which there are a plurality of regions of the second ultrasound image, that is, in a case in which a plurality of regions of the swallowing residue are found in the first ultrasound image, the shape of the surrounding line may be a rectangle that encompasses the plurality of regions of the second ultrasound image, for example, a circumscribed rectangle. Such a change in the shape of the surrounding line can be applied to all embodiments in which the graphic including the region of the second ultrasound image is superimposed on the second ultrasound image and displayed on the monitor 34.

The display control unit 33 may or may not display the surrounding line on the monitor 34. In a case in which the surrounding line is displayed, as the graphic, the region inside the surrounding line may be displayed with the second ultrasound image as it is, be subjected to predetermined hatching, be colored in a translucent color such that the second ultrasound image as a background can be visually recognized, or be displayed with a diagonal line. On the other hand, in a case in which the surrounding line is not displayed, the graphic may be subjected to predetermined hatching, be colored in a translucent color, or be displayed with a diagonal line, in the region of the second ultrasound image.

A case in which the display control unit 33 causes the monitor 34 to display the surrounding line surrounding the region of the swallowing residue in the first ultrasound image is the same as a case in which the display control unit 33 causes the monitor 34 to display the surrounding line surrounding the region of the second ultrasound image. In addition, a surrounding line correction unit may be provided, and after the surrounding line surrounding the region of the swallowing residue in the first ultrasound image is displayed on the monitor 34, the surrounding line surrounding the region of the swallowing residue may be corrected by the surrounding line correction unit in response to an instruction from the user. Further, the surrounding line surrounding the region of the swallowing residue in the first ultrasound image may or may not be displayed.

Further, the residue detection unit 62 may use the region of the swallowing residue in the first ultrasound image at the time of the past examination of the same subject as the region of the swallowing residue in the first ultrasound image at the time of the current examination of the same subject in a case in which no swallowing residue is detected in the first ultrasound image. In this case, the registration unit 66 performs registration of the first ultrasound image at the time of the past examination of the same subject, which is stored in the first ultrasound image memory 64, with respect to the second ultrasound image. As a result, even in a case in which no swallowing residue is detected in the first ultrasound image at the time of the current examination, the registration can be performed using the region of the swallowing residue in the first ultrasound image at the time of the past examination.

The place where the first ultrasound image at the time of the past examination of the same subject is stored may be in the first ultrasound image memory 64, that is, in the ultrasound diagnostic apparatus, or may be in an external server. In a case in which the first ultrasound image at the time of the past examination of the same subject is stored in the external server, the ultrasound diagnostic apparatus can use the terminal side communication circuit 32 to acquire the first ultrasound image at the time of the past examination of the same subject from the external server via the network.

In addition, the display control unit 33 may cause the monitor 34 to display the graphic including the region of the swallowing residue in the first ultrasound image at the time of the past examination of the same subject by superimposing the graphic on the first ultrasound image at the time of the current examination of the same subject. In this case as well, the display control unit 33 causes the monitor 34 to display the graphic including the region of the swallowing residue in the first ultrasound image at the time of current examination of the same subject by superimposing the graphic on the second ultrasound image at the time of the current examination of the same subject. As a result, the user can visually confirm the region having a probability of being the swallowing residue even when the ultrasound image of the right pharyngeal part is being captured.

Further, the region determination unit 68 may determine the region of the second ultrasound image at the time of the current examination of the same subject, on the basis of the region of the swallowing residue in the first ultrasound image at the time of the past examination of the same subject and the region of the swallowing residue in the first ultrasound image at the time of the current examination of the same subject. Alternatively, the region determination unit 68 may determine the region of the second ultrasound image at the time of the current examination of the same subject, on the basis of the region of the second ultrasound image corresponding to the region of the swallowing residue in the first ultrasound image at the time of the past examination of the same subject and the region of the swallowing residue in the first ultrasound image at the time of the current examination of the same subject. In this case, the display control unit 33 causes the monitor to display the graphic including the region of the second ultrasound image at the time of the current examination of the same subject by superimposing the graphic on the second ultrasound image at the time of the current examination of the same subject. As a result, the user can visually confirm the site where the swallowing residue is likely to remain and can determine whether or not the dysphagia is improved, from the region of the swallowing residue in the first ultrasound image at the time of the past and current examinations.

In a case in which the surrounding line surrounding the region of the second ultrasound image at the time of the current examination of the same subject is displayed, two surrounding lines corresponding to the region of the swallowing residue in the first ultrasound image at the time of the past examination of the same subject or the region of the second ultrasound image at the time of the past examination of the same subject, and the region of the swallowing residue in the first ultrasound image at the time of the current examination of the same subject may be separately displayed, for example, using at least one of different brightness, different colors, or different line types, or one surrounding line that encompasses the regions inside these two surrounding lines may be displayed.

After the region of the second ultrasound image is determined, the residue detection unit 62 may detect the region of the swallowing residue in the second ultrasound image by analyzing the image of the region of a predetermined shape that encompasses the region of the second ultrasound image. In this case, instead of the surrounding line surrounding the region of the second ultrasound image, the surrounding line surrounding the region of the swallowing residue in the second ultrasound image is superimposed on the second ultrasound image and displayed on the monitor 34. As a result, it is possible to suppress erroneous detection of the region of the swallowing residue in the second ultrasound image.

The registration, the determination of the region of the second ultrasound image, and the superimposition and display of the graphic including the region of the second ultrasound image described above can be repeatedly performed for the second ultrasound image (video image), that is, each of the plurality of continuous frames of the second ultrasound image.

In this case, performing the registration of the first ultrasound image with respect to the second ultrasound image through the registration unit 66, determining the region of the second ultrasound image corresponding to the region of the swallowing residue in the first ultrasound image, in which the registration has been performed with respect to the second ultrasound image, through the region determination unit 68, and updating the graphic including the region of the second ultrasound image, which is displayed on the monitor 34 by being superimposed on the second ultrasound image, through the display control unit 33 are repeatedly performed for each of the plurality of continuous frames of the second ultrasound image.

Meanwhile, in a case in which the calculation load related to the registration is high, for example, in a case in which the scanning of the second ultrasound image is delayed because of the calculation load related to the registration and an inappropriate second ultrasound image is generated, the registration, the determination of the region of the second ultrasound image, and the superimposition and display of the graphic including the region of the second ultrasound image described above may be performed for every predetermined number of frames of the second ultrasound image, rather than being repeatedly performed for each of the frames of the second ultrasound image.

In this case, performing the registration of the first ultrasound image with respect to the second ultrasound image through the registration unit 66, determining the region of the second ultrasound image corresponding to the region of the swallowing residue in the first ultrasound image, in which the registration has been performed with respect to the second ultrasound image, through the region determination unit 68, and updating the graphic including the region of the second ultrasound image, which is displayed on the monitor 34 by being superimposed on the second ultrasound image, through the display control unit 33 are repeated for every predetermined number of frames of the second ultrasound image among the plurality of continuous frames of the second ultrasound image.

As a result, it is possible to reduce the calculation load related to the registration, and it is possible to generate an appropriate second ultrasound image.

The region determination unit 68 may once determine the region of the second ultrasound image corresponding to the region of the swallowing residue in the first ultrasound image at the time of the current or past examination in which the registration has been performed with respect to the second ultrasound image, and then determine a region of the second ultrasound image in a subsequent frame corresponding to a region of the second ultrasound image in a previous frame, in adjacent frames of the second ultrasound image.

In this way, by determining the region of the second ultrasound image in the subsequent frame corresponding to the region of the second ultrasound image in the previous frame, it is possible to more accurately determine the region of the second ultrasound image than in a case of performing the registration of the first ultrasound image with respect to the second ultrasound image and determining the region of the second ultrasound image corresponding to the region of the swallowing residue in the first ultrasound image.

Further, an external server may be provided, and the external server may be configured to execute some functions of the residue processing unit 35, for example, at least one function of the residue detection unit 62, the registration unit 66, or the region determination unit 68.

The present invention is similarly applicable not only to a handheld type ultrasound diagnostic apparatus but also to a stationary ultrasound diagnostic apparatus or a portable ultrasound diagnostic apparatus in which an information terminal is realized by a laptop type terminal device. In addition, the cine memory 22 may be provided only in the ultrasound probe 1, only in the information terminal 3, or in both the ultrasound probe 1 and the information terminal 3. Further, the image information data generation unit 19 may be provided in the ultrasound probe 1 or in the information terminal 3.

In the apparatus of the embodiment of the present invention, as the hardware configuration of the processing unit that executes various types of processing, such as the transmission/reception circuit 14, the signal processing unit 16, the image processing unit 17, the probe control unit 21, the display control unit 33, the residue processing unit 35, and the terminal control unit 36, dedicated hardware may be used, or various processors or computers executing programs may be used. Further, as the hardware configuration, such as the cine memory 22 and the first ultrasound image memory 64, dedicated hardware may be used, or a memory, such as a semiconductor memory, and a storage device, such as a hard disk drive (HDD) and a solid state drive (SSD), may be used.

The various processors include a central processing unit (CPU) which is a general-purpose processor that executes software (programs) to function as various processing units, a programmable logic device (PLD) which is a processor whose circuit configuration can be changed after manufacturing, such as a field programmable gate array (FPGA), and a dedicated electric circuit which is a processor that has a dedicated circuit configuration designed to perform specific processing, such as an application specific integrated circuit (ASIC).

One processing unit may be composed of one of these various processors or may be composed of a combination of two or more processors of the same type or different types, for example, a combination of a plurality of FPGAs, a combination of an FPGA and a CPU, or the like. In addition, a plurality of processing units may be composed of one of the various processors, or two or more of the plurality of processing units may be combined and composed using one processor.

For example, as typified by a computer, such as a client and a server, there is an aspect in which one or more CPUs and software are combined to constitute one processor and the processor functions as the plurality of processing units. In addition, as typified by a system on chip (SoC) or the like, there is an aspect in which a processor that realizes functions of an entire system including a plurality of processing units with one integrated circuit (IC) chip is used.

Further, as the hardware configuration of these various processors, more specifically, electric circuits (circuitry) in which circuit elements, such as semiconductor elements, are combined are used.

In addition, the method of the embodiment of the present invention can be implemented, for example, by a program for causing a computer to execute each step. Further, it is also possible to provide a computer-readable recording medium on which this program is recorded.

Although the present invention has been described in detail above, the present invention is not limited to the above-described embodiment, and needless to say, various modifications or changes may be made without departing from the gist of the present invention.

EXPLANATION OF REFERENCES

1: ultrasound probe
3: information terminal
11: transducer array
14: transmission/reception circuit
16: signal processing unit
17: image processing unit
18: probe side communication circuit
19: image information data generation unit
21: probe control unit
22: cine memory
24: battery
25: probe side processor
32: terminal side communication circuit
33: display control unit
34: monitor
35: residue processing unit
36: terminal control unit
37: input device
39: terminal side processor
51: pulsar
52: amplification unit
53: AD conversion unit
54: beam former
60: image selection unit
62: residue detection unit
64: first ultrasound image memory
66: registration unit
68: region determination unit
70: warning unit

What is claimed is:

1. An ultrasound diagnostic apparatus comprising:
an ultrasound probe;
a monitor; and
a processor configured to:
generate a first ultrasound image of one of a left pharyngeal part and a right pharyngeal part of a subject, from a first reception signal obtained by transmitting and receiving a first ultrasound beam to and from the subject using the ultrasound probe;
analyze the first ultrasound image to detect a residue region representing a swallowing residue imaged in the first ultrasound image;
generate a second ultrasound image of the other of the left pharyngeal part and the right pharyngeal part of the subject, from a second reception signal obtained by transmitting and receiving a second ultrasound beam to and from the subject using the ultrasound probe;
perform registration of the first ultrasound image with respect to the second ultrasound image;
specify a residue candidate region disposed at a position in the second ultrasound image corresponding to a position of the residue region in the first ultrasound image; and
superimpose a first graphic indicating the residue candidate region on the second ultrasound image on the monitor.

2. The ultrasound diagnostic apparatus according to claim 1,
wherein the processor is further configured to perform the registration of the first ultrasound image whose left and right are inverted, with respect to the second ultrasound image.

3. The ultrasound diagnostic apparatus according to claim 2, further comprising:
an input device configured to input an instruction of a user;
wherein the processor is further configured to select the first ultrasound image from among a plurality of frames of ultrasound images of the one pharyngeal part in response to an instruction from the user input via the input device.

4. The ultrasound diagnostic apparatus according to claim 2,
wherein the processor is configured to use a residue region in the first ultrasound image at a time of a past examination of the same subject as the residue region in the first ultrasound image at a time of a current examination of the same subject in a case in which no swallowing residue is detected in the first ultrasound image.

5. The ultrasound diagnostic apparatus according to claim 2,
wherein the processor is further configured to
superimpose a second graphic including a residue region in the first ultrasound image at a time of a past examination of the same subject on the first ultrasound image at a time of a current examination of the same subject, on the monitor.

6. The ultrasound diagnostic apparatus according to claim 1, further comprising:
an input device configured to input an instruction of a user;
wherein the processor is further configured to select the first ultrasound image from among a plurality of frames of ultrasound images of the one pharyngeal part in response to an instruction from the user input via the input device.

7. The ultrasound diagnostic apparatus according to claim 1,
wherein the processor is configured to use a residue region in the first ultrasound image at a time of a past examination of the same subject as the residue region in the first ultrasound image at a time of a current examination of the same subject in a case in which no swallowing residue is detected in the first ultrasound image.

8. The ultrasound diagnostic apparatus according to claim 1,
wherein the processor is further configured to
superimpose a second graphic including a residue region in the first ultrasound image at a time of a past examination of the same subject on the first ultrasound image at a time of a current examination of the same subject, on the monitor.

9. The ultrasound diagnostic apparatus according to claim 1,
wherein the processor is further configured to
specify the residue candidate region in the second ultrasound image at a time of a current examination of the same subject, on the basis of a residue region in the first ultrasound image at a time of a past examination of the same subject or a residue candidate region in the second ultrasound image at the time of the past examination of the same subject, and the residue region in the first ultrasound image at a time of a current examination of the same subject, and superimpose a graphic including the residue candidate region at the time of the current examination of the same subject on the second ultrasound image at the time of the current examination of the same subject, on the monitor.

10. The ultrasound diagnostic apparatus according to claim 1,
wherein the processor is further configured to issue a warning in a case in which the registration of the first ultrasound image with respect to the second ultrasound image has failed.

11. The ultrasound diagnostic apparatus according to claim 1,
wherein the processor is further configured to analyze a partial image region that encompasses the residue candidate region in the second ultrasound image to detect the swallowing residue in the second ultrasound image.

12. The ultrasound diagnostic apparatus according to claim 1,
wherein the processor is further configured to repeat, for each of a plurality of continuous frames of the second ultrasound image,
performing the registration of the first ultrasound image with respect to the second ultrasound image,
specifying the residue candidate region in the second ultrasound image corresponding to the residue region in the first ultrasound image, and
updating the first graphic indicating the residue candidate region in the second ultrasound image, which is displayed on the monitor by being superimposed on the second ultrasound image.

13. The ultrasound diagnostic apparatus according to claim 12,
wherein the processor is further configured to once determine the residue candidate region in the second ultrasound image corresponding to the residue region in the first ultrasound image, and then specify a residue candidate region in the second ultrasound image in a subsequent frame corresponding to the residue candidate region in the second ultrasound image in a previous frame, in adjacent frames of the second ultrasound image.

14. The ultrasound diagnostic apparatus according to claim 1,
wherein the processor is further configured to repeat, for every predetermined number of frames of the second ultrasound image among a plurality of continuous frames of the second ultrasound image,
performing the registration of the first ultrasound image with respect to the second ultrasound image,
specifying the residue candidate region in the second ultrasound image corresponding to the residue region in the first ultrasound image, and updating the first graphic indicating the residue candidate region in the second ultrasound image, which is displayed on the monitor by being superimposed on the second ultrasound image.

15. The ultrasound diagnostic apparatus according to claim 1, further comprising:
a memory configured to store the first ultrasound image and the residue region in the first ultrasound image in association with each other.

16. The ultrasound diagnostic apparatus according to claim 1,
wherein the graphic is a surrounding line surrounding the residue candidate region in the second ultrasound image.

17. The ultrasound diagnostic apparatus according to claim 16,
wherein the residue candidate region inside the surrounding line is displayed with the ultrasound image as it is, is subjected to predetermined hatching, is colored in a translucent color, or is displayed with a diagonal line.

18. The ultrasound diagnostic apparatus according to claim 1,
wherein the graphic is a surrounding line of a predetermined shape that encompasses the residue candidate region in the second ultrasound image.

19. The ultrasound diagnostic apparatus according to claim 1,
wherein the first graphic is subjected to predetermined hatching, is colored in a translucent color, or is displayed with a diagonal line, in the residue candidate region in the second ultrasound image.

20. A control method for an ultrasound diagnostic apparatus, comprising:
generating a first ultrasound image of one of a left pharyngeal part and a right pharyngeal part of a subject, from a first reception signal obtained by transmitting and receiving a first ultrasound beam to and from the subject using an ultrasound probe;
analyzing the first ultrasound image to detect a residue region representing a swallowing residue imaged in the first ultrasound image;
generating a second ultrasound image of the other of the left pharyngeal part and the right pharyngeal part of the subject, from a second reception signal obtained by transmitting and receiving a second ultrasound beam to and from the subject using the ultrasound probe;
performing registration of the first ultrasound image with respect to the second ultrasound image;
specifying a residue candidate region disposed at a position in the second ultrasound image corresponding to a position of the residue region in the first ultrasound image; and
superimposing a first graphic indicating the residue candidate region in the second ultrasound image on the second ultrasound image on a monitor.

* * * * *